United States Patent [19]

Ericsson

[11] 4,007,087

[45] Feb. 8, 1977

[54] SPERM FRACTIONATION AND STORAGE

[75] Inventor: Ronald J. Ericsson, Sausalito, Calif.

[73] Assignee: Gametrics Limited, Sausalito, Calif.

[22] Filed: Oct. 17, 1975

[21] Appl. No.: 623,543

[52] U.S. Cl. .................................. 195/1.8; 424/105
[51] Int. Cl.² ................... C12K 9/00; A61K 35/52
[58] Field of Search ..................... 195/1.8; 424/105

[56] References Cited

UNITED STATES PATENTS

| | | | |
|---|---|---|---|
| 3,791,384 | 2/1974 | Richter et al. | 195/1.8 |
| 3,816,249 | 6/1974 | Bhattacharya | 195/1.8 |

Primary Examiner—Sam Rosen
Attorney, Agent, or Firm—Millen & White

[57] ABSTRACT

The percentage of the motile sperm of semen which survives frozen storage is increased by a process wherein the motile sperm is separated from the immotile sperm and the non-sperm components of the semen prior to storage. An insulated collection kit for collecting semen protects the semen from the adverse effects of handling and thermal shock.

13 Claims, No Drawings

SPERM FRACTIONATION AND STORAGE

BACKGROUND OF THE INVENTION

This invention relates to a method for reducing the loss in the fertility of semen upon storage and to a collection kit for collecting semen which protects the semen from the effects of handling and thermal shock.

Although the total number of sperm in an ejaculate is a measure of the fertility thereof, a more important criteria is the percentage of sperm thereof which are motile.

Sperm is conventionally catagorized according to the motility thereof on a scale of 0 – 4 as shown below.

| Degree of Motility | Type of Motility |
|---|---|
| 0° = | No motility — at most only tail movements without forward progression. |
| 1° = | 20% or less showing progression (generally sluggish swimming movements). |
| 2° = | 20 to 50% showing progression (generally good progressive swimming movements). |
| 3° = | 50 to 80% showing progression (usually rapid swimming movements). |
| 4° = | 80% and higher showing progression (usually very rapid swimming movements). |

A plus (+) following the number means the percentage is nearer the upper than the lower limit of the percentage range.

The proportion of motile sperm showing progressive swimming movements is a measure of the fertility of the sperm sample, i.e., the likelihood that the sample will achieve fertilization. Marginally fertile semen contains an abnormally low percentage of sperm exhibiting progressive swimming movements and generally is rated 0° or 1° in the above scale.

Thus, although total sperm count is one criteria of the fertility of a sperm sample, a more important indicia of its fertility is the proportion of the sperm which exhibits progressive swimming movements. The proportion of progressively motile sperm is important because not only is it an indication of the amount of fertile sperm in the sample, it is also a measure of the quality of the sperm, i.e., a sperm sample of high quality is more likely to achieve fertilization than a sperm sample of poor quality containing the same total number of motile sperm because the high proportion of dead sperm and their decomposition products in the latter appear to inhibit fertilization.

In my prior application Ser. No. 531,728, filed Dec. 11, 1974, whose disclosure is incorporated by reference, there is disclosed a method for separating motile sperm from immotile sperm by maintaining at least the sperm portion of progressively motile sperm-containing semen, either as such or preferably as a suspension in an aqueous vehicle physiologically acceptable to the sperm, as an upper layer in vertical interfacial contact with a discrete lower layer of an aqueous contacting medium physiologically acceptable to the sperm in which the motile sperm has a lower migration rate than in the upper layer, until motile sperm of the semen have migrated into the contacting medium, thereby producing a contacting medium containing a sperm fraction having a higher proportion of motile sperm with enhanced Y-sperm content. Repeating the process with the thus-obtained sperm fraction and a second contacting medium in which the motile sperm have a still lower migration rate than in the first contacting medium, produces a sperm fraction consisting predominantly of motile Y-sperms.

Motile sperm is separated from immotile sperm in the first fractionation, thereby providing a highly motile sperm fraction of enhanced content of motile Y-sperm and normal morphology, thereby greatly enhancing the quality of the sperm.

In the process of my prior applications, the quality of the sperm is improved to such an extent that the motile-sperm-containing fraction can be introduced directly into the human uterus, thus further increasing the likelihood of a successful insemination. This is also important in artificial insemination of animals, e.g., mares and cows, where today diluted stored semen is introduced directly in the uterus. Although the incidence of unsuccessful inseminations is relatively low, a significant number of inseminations are unsuccessful and require repeat insemination, resulting in economic loss to the owner of the animal due to the delay in pregnancy and to the inseminator who must repeat the insemination. It is believed these unsuccessful inseminations are at least partially due to the introduction into the uterus of animals stored semen containing a high proportion of immotile, defective and dead sperm and their decomposition products. The separation process of that application reduces insemination failures resulting from the introduction into the animal's uterus of such undesirable components of semen.

However, total motile sperm count is also a relevant factor in determining sperm quality as well as the proportion thereof which have progressive movements. In animal inseminations, where the dilutability of semen is an important economic factor, and in marginally fertile human semen, where the total sperm count is often far below normal values, the total number of live sperm remaining after processing is an important factor in determining the likelihood of a successful insemination, i.e., residual total live sperm count as well as the quality of the sperm must be considered in any method involving handling and storage of the sperm. Therefore, the total number of motile sperm with progressive movements which survive storage is an important factor as well as the quality of sperm, i.e., the proportion of such sperm remaining after processing.

It is well known that, especially with human sperm, a substantial portion of the motile sperm originally present in a sample of semen become immotile and/or die upon freezing. See, e.g., Smith, K. D. and Steinberger, E., "Survival of Spermatozoa in a Human Sperm Bank: Effects of Long-term Storage," J.A.M.A. 223:774, 1973; Steinberger, E. and Smith, K. D., "Artificial Insemination with Fresh or Frozen Semen: A Comparative Study," J.A.M.A. 223:778, 1973. These losses are usually less with domestic animals and are tolerated because it is usually impractical or impossible to use collected semen fast enough to store it in an unfrozen state. Because of such large losses of motile sperm on freezing, the freezing of a plurality of samples of marginally fertile human semen and pooling them in order to obtain a high enough total motile sperm count to increase the chances of insemination was not feasible because even though the total motile sperm count of the pooled sample might be brought up to normal ranges, the ratio of motile sperm to immotile sperm therein would be unacceptable, i.e., the quality of the sperm would be too low for insemination purposes.

It is also known that handling of semen in an unfrozen state and subjecting it to rapid temperature changes reduces the motile sperm count thereof. With donors having normal motile sperm counts, such losses are not serious. However, when attempting to achieve pregnancy by artificial insemination, using the semen of the marginally fertile husband, such losses due to handling and/or temperature shock are intolerable and usually precludes the use of the husband's semen for artificial insemination purposes.

It is an object of this invention to provide a process for storing sperm in a frozen state which reduces the loss of motile sperm resulting from storage.

It is another object to provide a collection container for semen which reduces motile sperm losses in unstored semen due to handling and/or thermal shock.

Other objects will be apparent to those skilled in the art.

SUMMARY OF THE INVENTION

In a process aspect, this invention relates to a process for reducing the loss in quality resulting from storing sperm in a frozen state, which comprises separating the motile sperm from the other components of semen and storing the separated motile sperm.

In an article of manufacture aspect, this invention relates to collection containers for unfrozen semen which reduces motile sperm losses due to handing or thermal shock.

DETAILED DISCUSSION

It was surprising to discover that the fertility of stored semen is significantly enhanced if the semen is fractionated to separate motile sperm from the other components thereof prior to storage. Whereas the quality, i.e., the proportion therein of sperm with progressive movements, of stored semen is enhanced by such a fractionation after storage, fertility loss upon storage, i.e., the loss upon storage both in the quality of the semen and the number of motile sperm with progressive movements initially present in the semen prior to storage, is reduced in the process of this invention.

It is surprising, since some losses of motile sperm occur in the fractionation step, that the overall yield of motile sperm after storage is higher when storage is preceded by fractionation. Nevertheless, assuming a reasonable effort is made in the fractionation step to recover as much as possible of the progressively motile sperm present in the starting sample of sperm, the overall recovery of progressively motile sperm after freezing is higher than if the whole semen is frozen. This means the stored semen of domestic animals can be diluted more, thereby increasing the number of inseminations per ejaculate. It also means that storage of marginally fertile human semen for pooling purposes is feasible because the overall recovery of motile sperm and the fertility of the recovered sperm is higher than when the sperm is stored without prior fractionation.

SPERM COLLECTION

In an article of manufacture aspect, this invention relates to a sperm collection container which reduces sperm motility loss due to handling and to thermal shock. Such a collection container comprises a conventional inert clear plastic centrifuge tube of about 15 ml. capacity (about 4¾ × ⅝ inch) preferably graduated for measuring the contents thereof, having a conical lower end, e.g., of about 1 ml. capacity and a threaded upper end; an inert threaded closure device, e.g., a plastic cap adapted to close the upper end of the tube; a semen receiving funnel, e.g., formed of inert plastic, with an internally threaded base adapted to be thread mounted on the top of the centrifuge tube; an insulating sleeve, preferably of polystyrene foam, open at one end and having a bore therein to receive and enclose the centrifuge tube, with its cap projecting therefrom; and an insulating cover (2¾ × 3⅝), also formed of polystyrene foam, with a stepped bore ending 1 inch from its top, adapted to fit over the cap of the centrifuge tube and onto sleeve. The insulating sleeve and cover are dimensioned so as to minimize the temperature gradient of the semen in the tube while in the covered sleeve and to minimize the rate temperature change thereof if the covered sleeved and closed centrifuge tube is temporarily stored in the refrigerator (0°–5° C.) or exposed to elevated temperatures (up to 40° C.) prior to or while being transported to the site of sperm fractionation and storage. With conventional styrofoam, in order to keep semen temperature fluctuations to less than 1° C. after reaching ambient temperature, the thickness of the insulation of the sleeve is preferably at least 2.25 times the radius of the centrifuge tube. Preferably, also, the sleeve is dimensioned so as to maintain the centrifuge tube in the sleeve in an upright position, e.g., a cylinder about 4⅝ inches in height and 3⅝ inches in diameter with a hollow bore (about ⅝ × 3⅝) ending 1 inch from the bottom adapted to receive the centrifuge tube.

Such a collection container can also be used to separate the sperm from the seminal fluid by centrifugation, to fractionate the motile sperm from the immotile sperm, and/or to dilute the sperm sample, thereby minimizing losses due to handling as well as reducing the likelihood of contamination.

SPERM FRACTIONATION

The sperm fraction step is based upon the discovery that the progressively motile sperm content of semen having an abnormally low proportion of progressive motile sperm can be selectively fractionated therefrom in high yield to produce a high quality sperm fraction having a substantially enhanced progressively motile sperm content and a greatly reduced content of non-progressively motile and immotile sperm, morphologically and genetically abnormal sperm, dead sperm and their decomposition products and non-sperm semen components, e.g., round cells, particulate material, etc.

Whereas progressively motile and immotile sperm suspended in, e.g., isotonic saline or Tyrode solution, both settle downwardly therein at substantially the same rate, if a suspension of semen containing progressively motile sperm in a suspending vehicle which does not substantially retard downward mitration rate is vertically layered on top of a discrete lower layer of a contacting medium which does retard the migration rate of the semen, the progressively motile sperm will migrate downwardly through the contacting medium, leaving most or all of the non-progressively motile, immotile and morphologically adnormal sperm and other non-sperm semen components behind.

In the fractionation step of the process of this invention, the proportion of progressively motile sperm can be increased from 70% or far less, in the case of marginally fertile or stored sperm, to 90–95% or higher. If desired, a sperm fraction having substantially enhanced Y-sperm content can also be produced in this step of the process of this invention by repeating the fractionation step with the thus-obtained sperm fraction and a second contacting medium which retards migration rate more than the first contacting medium. This further enhances the Y-sperm content of the sperms migrating thereto, so that sperm fractions having a 70–90% or more Y-sperm content can be obtained.

It will be appreciated that enhancing the progressively motile sperm content of the thus-obtained sperm fractions causes a corresponding decrease in total number of sperm recovered, primarily from the reduction in its non-progressively motile sperm content but also to a lesser extent from the loss of the progressively motile sperms which have not yet migrated into the contacting medium when the fractionation step is terminated. However, the recovery of progressively motile sperm is surprisingly high. The loss of progressively motile sperm is compensated for by the improved quality of the resulting sperm sample, since the chances of a successful impregnation therewith are greater than a starting sample of poorer quality semen having a higher total sperm count. Finally, as stated above, because of the high quality of the resulting sperm sample, impregnation directly into the human uterus is clinically more acceptable, thereby further increasing the chances of fertilization.

The process of the invention can be used with the semen of all mammals. Of special interest is the semen of animals which are used in agriculture or for other economic purposes, for example, horses, cattle, pigs, sheep, goats, rabbits, etc. The process can also be used in the same manner with human semen, not only in cases of marginal sperm fertility and when it is desired to store the semen of normal donors, but also when a male child is desired.

The starting sperm from which the progressively motile sperm are fractionated are preferably and ordinarily dispersed in a vehicle physiologically acceptable to the sperm. Such a vehicle is nontoxic to the sperm and does not weaken the fertility of the sperm, i.e., it must neither harm nor destroy the sperm. Such a vehicle has a pH-value within the range of about 6 to 8 which is compatible with the semen and an osmotic pressure at which the sperms are not compressed or disintegrated.

Because the fractionation step involves the migration of progressively motile sperm into a aqueous contacting medium which retards the sperm migration rate, the aqueous vehicle in which the sperm are suspended in the initial fractionation step ordinarily should not significantly retard the sperm migration rate, in order to avoid interfering with the migration of the progressively motile sperm from the suspending vehicle into the contacting medium. Such vehicles have a density close to that of water, i.e., about 1.001 to 1.100 g/ml., preferably about 1.005 to 1.070 g/ml. Preferably such solutions also have a low viscosity, viz., about that of water. However, the fractionation step of the process of this invention is based upon the use of a contacting medium as a lower layer in which the progressively motile semen migrate at a slower rate than the rate at which they migrate in the upper layer, i.e., the process is based upon a migration rate differential between the upper and lower layers. Therefore, while it is preferable that the suspending vehicle be one which does not retard the migration of progressively motile sperm, because higher recoveries of progressively motile sperm are achieved with such suspending vehicles, those which do retard migration rates can be used as long as the contacting medium retards the migration rate even more so. Moreover, in one aspect of the fractionation step of the process of this invention, the first contacting medium acts as a suspending vehicle and is layered above a second contacting medium.

Thus, it is possible to employ whole semen in the upper layer, either as such or diluted with a physiologically acceptable suspending vehicle. However, because whole semen is viscous even when diluted, the contacting medium must be correspondingly more viscous to provide the requisite retardation of downward migration rate of the progressively motile sperm. As a consequence, lower recoveries of the progressively motile sperm present in the semen is realized. Therefore, it is preferable to separate the sperm from the seminal fluid, usually after dilution with a physiologically acceptable suspending vehicle, e.g., be centrifugation, and resuspend the sperm in fresh suspending vehicle before conducting the fractionation process.

Examples of aqueous solutions which are physiologically acceptable to the semen and can thus be used as suspending vehicles and contacting media are well known in the art and include solutions such as, for example, Tyrode solution, Ringer solution, Hanks' solution, isotonic sodium chloride solutions, Medium 199, Eagle's Medium, etc. The density and/or viscosity of these solutions can be increased by the addition thereto of an additive described hereinafter which can be present in the contacting medium.

The contacting medium can be entirely different in composition from the aqueous suspending vehicle, so long as both are physiologically acceptable to the sperm. However, they can be and preferably are essentially the same solutions, e.g., Tyrode solution, with the contacting medium containing an additional ingredient or a larger amount of a common ingredient, which retards significantly the migration rate of the progressively motile sperm compared to their settling rate in the suspending vehicle. As stated above, such an ingredient ordinarily increases both the density and the viscosity of the contacting medium.

Aqueous contacting media which retard the migration rate of progressively motile sperm compared to the suspending vehicle generally have significantly higher densities and viscosities than water, isotonic saline solutions, Tyrode solution and other solutions suitable as suspending vehicles. It is theoretically possible to increase the density of the contacting medium without simultaneously significantly increasing its viscosity. Similarly, polymers which form a sol or gel can greatly increase viscosity and have little effect upon density. However, as a practical matter a contacting medium which retards migration rate and is physiologically acceptable to the sperm generally has both higher density and viscosity than a suspending vehicle which does not retard migration rate. In any event, whether the lowering of the migration rate of the progressively motile sperm in the contacting medium is the result of the latter's higher density, higher viscosity, or both, is not critical as long as the migration rate of the progressively motile sperm is reduced.

As stated above, the contacting medium, in addition to retarding the migration rate of the sperm, should meet the criteria mentioned above for the suspending vehicle of low density in which the semen may be dispersed, i.e., it must be physiologically acceptable to the sperm. Thus, there may be employed any physiologically acceptable solution in which sperm can be maintained in a viable and motile state, for example, those mentioned above as suspending vehicles, which are adapted by means of soluble materials known to pharmacologists and physiologists to the desired condition of higher density and/or viscosity. Such additives include, for example, salts, low molecular and high molecular weight organic compounds, e.g., mon-and oligo-saccharides, amino-acids, peptides, proteins, proteids and synthetic polymers, for example, polyvinylpyrrolidone.

Specific examples of such soluble materials are:

PROTEINS
Albumins
  Bovine Serum Albumin (3–25%) Density: 1.012–1.075 g/ml.
  Human Serum Albumin
  Ovalbumin (6–15%) Density: 1.018–1.041
Globulins
  Alpha Bovine Globulin (10%) Density (1.028)
  Human and other alpha globulins
  Beta Globulins      Thrombin
  Gamma Globulins     Hemoglobin
  Glyco proteins      Casein
  Fibrinogen          Lactoglobulins
  Prothrombin         Lactalbumins

| AMINO ACIDS | PEPTIDES | SACCHARIDES |
|---|---|---|
| Alanine | L-Alanyl-L-Aline | Monosaccharides |
| Arginine | L-Alanyl-L-Lysine | Glucose |
| Cysteine | L-Alanyl-L-Serine | Fructose |
| Glutamic Acid | Tri-L-Alanine | Disaccharides |
| Glycine | Hexa-L-Alanine | Maltose |
| Histidine | Glycyl-Glycine | Lactose |
| Hydroxyproline | Glycyl-L-Leucine | Sucrose |
| Leucine | L-Leucyl-L-Alanine | Polysaccharides |
| Lysine | L-Phenylalanyl-Glycine | Dextrans |
| Methionine | L-Seryl-Glycine | |
| Ornithine | L-Tyrosyl-L-Alanine | SALTS |
| Phenylalanine | | NaCl |
| Proline | | KCl |
| Serine | | MgCl |
| Tryptophan | | CaCl |
| Tyrosine | | $NaH_2PO_3$ |
| Valine | | $NaHCO_3$ |

An additive employed for achieving the desired retardation of sperm migration rate need not be completely soluble in the starting solution. Thus, high molecular weight proteins and synthetic polymers can be employed as a colloidal sol or gel.

Migration rate differential required to achieve the desired separation of progressively motile sperms from immotile sperms and to fractionate Y-sperms from semen is not critical and partially depends on the nature and quality of the mammal semen used and the additives present in the contacting medium to provide a density and/or viscosity differential between the upper and lower layers. For example, when using bovine serum albumin or other serum albumin or serum globulin protein, and a suspending vehicle which does not retard downward migration, the protein need be present in the contacting medium at a concentration of only about 1–5%, preferably about 3–5%, to achieve separation of progressively motile sperm from immotile sperm. However, to achieve optimum separation of progressively motile Y-sperm from progressively motile X-sperm, the protein should be present at a higher concentration in the final contacting medium, e.g., 3–50%, preferably about 10–25%.

The starting sperm which are preferably dispersed in a suspending vehicle and separated from seminal fluid, can be brought into contact with the contacting medium in any desired manner, so long as care is taken that mixing of the sperm layer with the layer of contacting medium does not occur. The preferred method of contacting is to overlay the contacting medium with the semen layer. However, it is also possible, with sufficient care, to underlay the sperm layer with a layer of the contacting medium. When the sperm, optionally dispersed in a suspending vehicle, is brought into contact with the contacting medium, a single contact leads to satisfactory separation of progressively motile from immotile sperm and significant enhancement of the Y-sperm content of the fractionated progressively motile sperm. However, the extent of Y-sperm content enhancement can be and preferably is increased by repeating the contacting step one or more times, i.e., contacting the sperm fraction which migrated to the first contacting medium with a second contacting medium in which the sperm have a lower migration rate than in the first contacting medium, i.e., one having a higher density (and/or viscosity).

When the sperm fractionation is repeated by underlaying the first contacting medium with a second contacting medium, the latter should be a solution which further retards the sperm migration rate, i.e., a solution in which the progressively motile sperm migrate at a lower rate than the rate at which they migrate in the first contacting medium.

The repeated contacting step can be carried out with a single contacting medium or with a plurality, for example, two or three, of contacting media of progressively higher density and/or viscosity, for example, by underlaying the dispersed starting sperm with the first contacting medium of higher density and then underlaying this solution with the second contacting medium.

The repeated contacting step can alternatively be carried out by first separating the sperm which have migrated to the contacting medium therefrom and contacting the separated sperm, resuspended in fresh suspending vehicle, with the second contacting medium in the same manner as in the first contacting step. A still further alternative is to separate the first contacting medium containing the separated sperm from the upper starting sperm layer and thereafter contacting the separated first contacting medium with a lower layer of second contacting medium.

For convenience, the process is usually conducted at room temperature but can be conducted at any higher or lower temperature at which the sperm can be maintained alive and motile, e.g., from about 15° C. to about the normal body temperature of the species of mammal whose sperm is being fractionated, viz., up to about 40° C., preferably about 20°–25° C. At elevated temperatures or when conducting the process for several hours, it is sometimes advantageous to incorporate into the suspending vehicle and contacting medium an antibiotic, e.g., tetracycline, a penicillin or gentamycin, or a bacteriostat which is physiologically acceptable to the sperm.

The time required for carrying out the isolation (or separation) depends on the species of mammal, the nature of the contacting medium and the type of isolation or separation used, the exact time not being critical. Very short times give poor motile sperm recoveries. Generally, contact times of 0.25 – 10.0, preferably 1.0 – 4.0 hours, are employed. A contact period of about 0.5 to 10 hours and preferably about 1 to 3 hours generally is sufficient to separate a high proportion of the progressively motile sperms from the immotile sperms and substantially increase the Y-sperm content of the progressively motile sperm which have migrated to the contacting medium.

The sperms in the final contacting medium can be recovered for storage by separating all or, if a lower recovery of progressively motile sperm can be tolerated, the lower fraction only of the final contacting medium, e.g., by carefully pipetting or decanting. The contacting medium containing the fractionated sperm can be used as such for insemination purposes after storage if the vehicle is suitable for such purpose, diluted to render it suitable for that purpose, or the sperm can be separated therefrom in a conventional manner, e.g., by centrifugation, and then resuspended for use in a suspending vehicle physiologically acceptable to the sperm and suitable as a vehicle for insemination purposes, e.g., Tyrodes solution.

The sperm fractionation step of the process of this invention can be carried out in vessels of any form, such as are customarily used by those skilled in the art for working with small quantities of fluids, for example, burettes, pipettes, separating tubes and columns having a suitable closure, etc. Any vertical elongate vessel with a sealed bottom is operable.

FREEZING STEP

The freezing step is conducted according to conventional techniques. See Sherman and Bunge. The whole semen or the separated sperm fraction thereof is diluted 1:1 with a freezing diluent, either glycerine or preferably the diluent described in the examples hereinafter, gently shaken to ensure thorough mixing, sealed in a suitable closed sterile container, preferably a flame sealed glass ampoule or an inert sealed plastic straw (tube), and then cooled to about $-70°$ to $-200°$ C., i.e., in dry ice or liquid nitrogen. The cooling preferably should be at the rate of about 10° to 15°/min. The frozen sperm optionally can be under an inert atmosphere, e.g., nitrogen.

The frozen sperm can then be stored until used, e.g., from a few weeks to several months or years.

THAWING AND USE

Because unfrozen sperm is damaged by handling and by thermal shock, the thawing and subsequent processing should be conducted so as to minimize these adverse effects. The sperm preferably should be brought to room temperature by immersing in a room temperature water bath.

When the fractionated sperm is frozen in the preferred freezing diluent of the examples hereinafter, it can be used directly for insemination without further processing, thus reducing losses due to handling. However, if desired, it can be centrifuged, the supernatant decanted and the sperm pellet resuspended in, e.g., Tyrode solution.

The fertility of a sperm sample is influenced by:
 a. motile sperm count (population);
 b. ratio of total sperm to motile sperm (environment); and
 c. progressiveness of motility of the motile sperm (viability).

Frozen sperm, particularly human sperm, suffers a loss in fertility by all three factors. Fractionation of frozen semen after thawing according to the process of Ser. No. 531,728 enhances the environment and viability of the fractionated sample of semen but does not, of course, avoid the loss in motile sperm count resulting from the effects of freezing. By the process of this invention, not only is the environment and viability of the fractionated sample enhanced, overall recovery of motile sperm after thawing usually is higher than with unfractionated sperm or sperm fractionated after storage.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following Examples, the temperatures are set forth at room temperature and uncorrected in degrees Celsius unless otherwise indicated, all parts and percentages are by weight. The values obtained in elemental analyses are within commonly accepted limits of error.

Before separation, the number and motility of the sperm is determined according to the procedure of C. Schirren (Praktische Andrologie, Verlag Bruder Hartmann, Berlin 1971). The subsequent isolation (or separation) is followed by determining X- and Y-sperm contents according to the quinacridine technique. Acta.Biol.Med. Germ, 28 (1972) 189–92. The sperm can be recovered by centrifuging.

The contact times were determined by the rate at which the progressively motile sperm migrated through the various contacting media. Normal progressively motile sperm migrate rapidly downward at room temperature through vehicles which do not retard migration rate, e.g., human, ca. 30–50 cm per hour. In 6% BSA, the migration rate is about one-tenth that, e.g., about 4–5 cm per hour. Generally speaking, contacting media are employed which lower migration rates to 1–50%, preferably about 5–25%, of the unretarded migration rate of the progressively motile sperm employed. When Y-sperm and X-sperm fractionation is desired, contacting times are selected which permit a portion only, e.g., from 5–75%, preferably 10–50%, of the motile sperm above the contacting medium to migrate thereto. As would be obvious, if the contact time is long enough to permit all or substantially all of the progressively motile sperm to migrate into the contacting medium below the sperm layer, significant Y-sperm and X-sperm fractionation will not occur unless the lower portion of the contacting medium is separated from the upper portion thereof before all of the progressively motile sperm have migrated to the bottom of the contacting medium. However, in the fractionation step of the process of this invention, Y- and X-sperm fractionation is not ordinarily sought and maximum progressively motile sperm recovery is desired. Therefore, contacting times long enough to achieve more than 75% progressively motile sperm recovery ordinarily are employed. The only limiting factors are the life span of the progressively motile sperm in the contacting medium and the settling rate of the non-progressively motile sperm downwardly into the contacting medium, which is about one-tenth the migration rate of motile sperm therein. When a plurality of contacting medium are employed, few immotile sperm penetrate the last contacting medium. EXAMPLES 1 – 16

Semen was collected from donors within 1–2 hours of use and transferred to capped plastic centrifuge tubes. All samples and all procedures (except freezing) maintained at room temperature. Semen volume was measured and then each sample, except for a 0.5 cc control aliquot, was diluted 1:1 with Tyrode solution. Sperm motility (both percentage motile and progressiveness of movement) and sperm numbers of each sample of semen were determined. Prior to diluting each semen sample, a 0.5 ml aliquot was removed and retained as a control for each of the semen samples. The control samples, of known sperm counts and motility, (as described in Examples 17–18) were mixed 1:1 with semen freezing diluent and frozen (dry ice). Temperature drop from room temperature to −80° to −100° C. required six minutes. After freezing for 15 minutes, the samples were submerged in a water bath at room temperature for 30–40 minutes. The plastic vials were then opened and the sperm checked for motility after freezing.

Each of the Tyrodes diluted samples was centrifuged for 15 minutes at approximately 3600 rpm. The resulting sperm pellet was separated from the supernatant seminal fluid and resuspended in volumes of Tyrodes which provided 50 – 100 × 10$^6$ sperm per ml. (Some samples had insufficient numbers of sperm to provide a concentration of 100 × 10$^6$ per ml.)

Fractionation columns were made from Pasteur pipettes, heat-sealed at the point of tapering, positioned vertically; the number of columns used being determined by the volume of the samples resulting from dilution to a 50–100 × 10$^6$ per ml. sperm concentration. A bottom liquid layer therein consisted of 0.5 ml of a 17.5% solution of BSA (buffered in Tyrodes). Overlayering this was 1.0 ml of a 7.5% solution of BSA. The top layer consisted of 0.5 ml of the centrifuged sperm in Tyrode solution. Sperm counts varied from 25 to 50 × 10$^6$.

The sperm layer was removed by pipette after one hour. The BSA layers were separated from one another by the same procedure after an additional 30 minutes. The top (sperm) layer and the two BSA layers were checked for percentage and progressiveness of sperm motility. The sperm in the 17.5% BSA layer were also counted, and, in some cases, in the 7.5% BSA layer also.

Sperm fractions from the 17.5% BSA layer were diluted 1:1 with Tyrodes. The numbers and motility of the sperm therein were then determined. The samples were then centrifuged for 10 minutes at 3,600 rpms and all but 0.3 ml of the liquid decanted. An equal amount of semen extender (0.3 ml except no. 1 where 0.5 ml was used) was then added to the remainder and the entire contents thoroughly mixed. The sperm motilities of both the control and the fractionated samples were rechecked immediately prior to freezing of each. The fractionated samples were placed in vials and frozen and rethawed by the same procedure employed for the control samples.

The results of the freezing are given in Tables 1 through 6, which give sperm survival, both before and after freezing. The data of Table 1 show that the fraction process produced fractions with better motility (higher in percentage and more progressive in movement) than controls. As shown in Table 2, the better motility of the fractionated samples was retained after the stress at freezing. As shown in Table 3, sperm from the 17.5% BSA fraction have a greater ability to servive freezing than do their own controls. Even though control samples initially had more total sperm, the fractionated samples (except No. 1) had more live sperm after thawing. Table 4, which gives the concentration of sperm used per column and the number of columns used, also gives the yield of initially motile sperm recovered in the 17.5% BSA fraction and provides a check of the success of the fractionation. Table 5 gives comparisons of survival rates of initially motile human sperm in the unfractionated semen, the 7.5% BSA and the 17.5% BSA fractions. Table 6 shows the effect of long-term storage upon motility.

TABLE 1

Percentage and Progressiveness of Motility of Human Sperm Subjected to the Fractionation.

| Semen Sample No. | SEMEN CONTROL | FRACTIONS | | |
|---|---|---|---|---|
| | | Top | 7.5% BSA | 17.5% BSA |
| 1 | 45% 3 | 5% 2+ | 40% 3 | 95% 3+ |
| 2 | 40% 2+ | 5% 2 | 75% 2+ | 90% 3 |
| 3 | 50% 2+ | 15% 2+ | 85% 3+ | 95% 4 |
| 4 | 40% 2+ | 5% 1+ | 80% 3+ | 95% 4 |
| 5 | 40% 2+ | 10% 2+ | — | 85% 4 |
| 6 | 70% 3 | 10% 2+ | 80% 3+ | 95% 4 |
| 7 | 35% 2+ | 5% 2+ | 70% 2+ | 95% 3+ |
| 8 | 25% 1+** | 10% 1+ | 70% 2+ | 85% 3+ |
| 9 | 50% 2+ | 5% 2 | 60% 3 | 95% 3+ |
| 10 | 60% 3+ | 5% 1+ | 80% 3+ | 80% 3+ |
| 11 | 65% 3 | 10% 2+ | 70% 3+ | 40%*2 |
| 12 | 70% 4 | 10% 3 | 80% 3+ | 90% 4 |
| 13 | 60% 3 | 10% 2+ | 80% 3+ | 90% 4 |
| 14 | 70% 3 | 40% 3+ | 80% 3 | 95% 3+ |
| 15 | 70% 3 | 30% 3 | 85% 3+ | 95% 4 |
| 16 | 40% 2 | 5% 1 | 70% 2+ | 80% 3 |
| 17 | 60% 3 | 5% 2+ | 90% 3 | 95% 3 |
| 18 | 70% 3 | 10% 2 | 80% 3+ | 85% 3+ |
| 19 | 50% 2+ | 10% 2+ | 60% 2 | 85% 3+ |
| 20 | 40% 3 | 15% 2 | — | 75% 3 |
| 21 | 45% 2+ | 15% 2+ | 50% 2+ | 80% 3 |
| 22 | 60% 3 | 10% 2 | 75% 3 | 95% 3+ |
| 23 | 50% 2 | 15% 3 | 75% 3+ | 90% 4 |
| 24 | 75% 4 | 10% 2 | 75% 3+ | 95% 4 |

*Large variation among slides
**May be poor slide

TABLE 2

Percentage and Progressiveness of Motility of Initially Motile Human Sperm Surviving Freezing (× 10$^6$)

| Semen Sample No. | SEMEN CONTROL | | | 17.5% BSA FRACTION | | |
|---|---|---|---|---|---|---|
| | Prefreeze | Post-thaw | Percent Survival* | Prefreeze | Post-thaw | Percent Survival* |
| 1 | 30 2 | 15 2 | 50 | 95 3+ | 50 3 | 53 |
| 2 | 40 3 | 20 2+ | 50 | 80 3 | 60 3 | 75 |
| 3 | 60 3 | 30 2+ | 50 | 80 3+ | 60 3+ | 75 |
| 4 | 40 2+ | 5 2 | 13 | 90 3+ | 75 3+ | 83 |
| 5 | 45 3 | 10 3 | 22 | 90 4 | 50 3 | 56 |
| 6 | 75 3+ | 45 3 | 60 | 90 4 | 70 3+ | 78 |
| 7 | 40 3 | 5 2 | 13 | 90 4 | 50 2 | 56 |
| 8 | 60 3+ | 15 2 | 25 | 80 3+ | 45 2+ | 56 |
| 9 | 65 3 | 20 2 | 31 | 70 3+ | 40 3 | 57 |
| 10 | 60 3+ | 25 2+ | 42 | 90 4 | 60 3+ | 67 |
| 11 | 60 3+ | 30 2+ | 50 | 65 3 | 55 3 | 85 |
| 12 | 60 3 | 20 2 | 33 | 85 4 | 70 4 | 82 |

TABLE 2-continued

| | | | | | | | | | | |
|---|---|---|---|---|---|---|---|---|---|---|
| 13 | 75 | 3+ | 40 | 3 | 53 | 85 | 4 | 60 | 3+ | 71 |
| 14 | 75 | 3+ | 10 | 3 | 13 | 95 | 4 | 60 | 3+ | 63 |
| 15 | 75 | 3+ | 40 | 2+ | 53 | 80 | 4 | 55 | 3 | 69 |
| 16 | 35 | 2+ | 1 | 1+ | 3 | 65 | 3 | 55 | 2+ | 85 |
| 17 | 65 | 3+ | 15 | 2 | 23 | 85 | 3 | 45 | 2+ | 53 |
| 18 | 70 | 3+ | 30 | 2+ | 43 | 85 | 4 | 60 | 3+ | 71 |
| 19 | 60 | 3 | 25 | 2 | 42 | 70 | 3 | 60 | 2+ | 86 |
| 20 | 40 | 3 | 10 | 1+ | 25 | 75 | 2+ | 50 | 2 | 67 |
| 21 | 50 | 2+ | 15 | 1+ | 30 | 80 | 3 | 40 | 2 | 50 |
| 22 | 65 | 3+ | 20 | 2+ | 31 | 85 | 4 | 70 | 3+ | 82 |
| 23 | 60 | 3 | 30 | 2 | 50 | 85 | 4 | 70 | 3+ | 82 |
| 24 | 70 | 3+ | 10 | 2 | 14 | 80 | 4 | 60 | 3+ | 75 |

*Percent of initially motile sperm which survive freezing.

| | 7.5% BSA FRACTION | | | | |
|---|---|---|---|---|---|
| 13 | 85% | 4 | 50% | 3+ | 59 |
| 14 | 65% | 3+ | 45% | 2+ | 69 |
| 16 | 75% | 3+ | 55% | 3+ | 73 |

TABLE 3

Numbers of Initially Motile Human Sperm Surviving Freezing ($\times 10^6$)

| Semen Sample No. | Total Sperm Count | Motile Sperm in SEMEN CONTROL | | Total Sperm Count | Motile Sperm in 17.5% BSA FRACTION | | Percent Recovery* |
|---|---|---|---|---|---|---|---|
| | | Prefreeze | Post-thaw | | Prefreeze | Post-thaw | |
| 1 | 25 | 7.5 | 3.8 | 4.2 | 4.0 | 2.1 | 52.6 |
| 2 | 114 | 45.6 | 4.7 | 49.6 | 44.6 | 37.2 | 83.4 |
| 3 | 35 | 15.7 | 3.5 | 10.4 | 9.4 | 5.2 | 53.4 |
| 4 | 20 | 8.0 | 1.0 | 10.5 | 9.5 | 5.3 | 55.9 |
| 5 | 39 | 23.4 | 9.8 | 32.0 | 28.8 | 19.2 | 66.7 |
| 6 | 60 | 45.0 | 6.0 | 36.0 | 34.2 | 21.6 | 63.2 |
| 7 | 32 | 11.2 | 0.3 | 12.0 | 7.8 | 6.6 | 84.7 |
| 8 | 28 | 18.8 | 4.4 | 11.2 | 9.5 | 5.0 | 52.7 |
| 9 | 36 | 21.6 | 10.8 | 42.3 | 27.5 | 23.3 | 84.8 |
| 10 | 37 | 15.2 | 7.6 | 15.6 | 13.3 | 9.4 | 70.6 |
| 11 | 19.2 | 11.5 | 4.8 | 4.2 | 2.8 | 2.4 | |
| 12 | 20.9 | 8.4 | 2.1 | 1.2 | 0.9 | 0.6 | |
| 13 | 24.6 | 18.5 | 11.1 | 12.0 | 10.8 | 8.4 | |
| 14 | 67.9 | 44.1 | 13.6 | 15.0 | 12.8 | 10.5 | |
| 15 | 5.4 | 3.2 | 0.8 | 3.2 | 2.6 | 1.4 | |
| 16 | 48.0 | 28.8 | 9.6 | 33.6 | 28.6 | 25.3 | |

*Percent Recovery of Initially Motile Sperm

| | 7.5% BSA FRACTION | | |
|---|---|---|---|
| 13 | 29 | 24.7 | 14.5 |
| 14 | 40.7 | 26.5 | 18.3 |
| 16 | 55.3 | 41.5 | 30.4 |

TABLE 4

Yield of Motile Human Sperm in the 17.5% BSA Fraction

| Semen Sample No. | Total No. of Sperm $\times 10^6$ in Sample | No. of Isolation Columns | Percent Recovery of Initially Motile Sperm |
|---|---|---|---|
| 1 | 50 | 2 | 18 |
| 2 | 400 | 8 | 12 |
| 3 | 70 | 2 | 32 |
| 4 | 79 | 2 | 36 |
| 5 | 400 | 8 | 11 |
| 6 | 300 | 6 | 16 |
| 7 | 200 | 4 | 12 |
| 8 | 104 | 3 | 17 |
| 9 | 432 | 9 | 10 |
| 10 | 136 | 3 | 26 |
| 11 | 96 | 3 | 7.4 |
| 12 | 100 | 3 | 2.3 |
| 13 | 108 | 3 | 15.1 |
| 14 | 312 | 6 | 7.6 |
| 15 | 32 | 2 | 14.1 |
| 16 | 336 | 7 | 12.9 |

TABLE 5

Percentage and Progressiveness of Motility of Initially Motile Human Sperm Surviving Freezing

| Semen Donor No. | SEMEN CONTROL | | | 7.5% BSA FRACTION | | | 17.5% BSA FRACTION | | |
|---|---|---|---|---|---|---|---|---|---|
| | Prefreeze | Post-thaw | Percent Survival | Prefreeze | Post-thaw | Percent Survival | Prefreeze | Post-thaw | Percent Survival |
| 1 | 60 3 | 30 2+ | 50 | 85 3+ | 55 3+ | 69 | 95 4 | 60 3+ | 75 |
| 3 | 75 3+ | 45 3 | 60 | 85 4 | 50 3+ | 59 | 90 4 | 70 3+ | 78 |
| 4 | 65 3 | 20 2 | 31 | 60 3 | 30 2+ | 50 | 95 3+ | 40 3 | 57 |
| 5 | 75 3+ | 40 3 | 53 | 80 3+ | 55 3+ | 69 | 90 4 | 60 3+ | 71 |
| 6 | 75 3+ | 40 2+ | 53 | 70 3+ | 40 3 | 57 | 80 4 | 55 3 | 69 |
| 8 | 70 3+ | 30 2+ | 43 | 70 3+ | 45 3 | 64 | 85 4 | 60 3+ | 71 |
| 10 | 50 2+ | 15 1+ | 30 | 50 2+ | 25 2 | 50 | 80 3 | 40 2 | 50 |

TABLE 5-continued

Percentage and Progressiveness
of Motility of Initially Motile
Human Sperm Surviving Freezing

| Semen Donor No. | SEMEN CONTROL | | | 7.5% BSA FRACTION | | | 17.5% BSA FRACTION | | |
|---|---|---|---|---|---|---|---|---|---|
| | Prefreeze | Post-thaw | Percent Survival | Prefreeze | Post-thaw | Percent Survival | Prefreeze | Post-thaw | Percent Survival |
| 11 | 65 3+ | 20 2+ | 31 | 65 3+ | 45 2+ | 69 | 85 4 | 70 3+ | 82 |
| 12 | 60 3 | 30 2 | 50 | 70 3+ | 55 3+ | 79 | 85 4 | 70 3+ | 82 |
| 13 | 70 3+ | 10 2 | 14 | 60 3+ | 40 3 | 67 | 80 4 | 60 3' | 75 |
| Average | | | 41 ± 14 | | | 64 ± 9 | | | 72 ± 10 |

TABLE 6

Percentage and Progressiveness of
Motility of Human Sperm
AFter Storage

| | Sperm Motility | | | | | | | | | |
|---|---|---|---|---|---|---|---|---|---|---|
| | Donor 1 | | Donor 2 | | Donor 3 | | Donor 4 | | Donor 11 | |
| Fractions | Pre-Freeze | Post-Thaw[1] | Pre-Freeze | Post-Thaw[2] | Pre-Freeze | Post-Thaw[3] | Pre-Freeze | Post-Thaw[4] | Pre-Freeze | Post-Thaw[11] |
| Semen Control | 75 4 | 20 3 | 65 3 | 20 2 | 80 4 | 30 3 | 70 4 | 15 3 | 75 4 | 45 4 |
| Top | 35 2+ | — | 30 2 | — | 40 3 | — | 50 4 | — | 15 4 | — |
| 6% BSA | 90 4 | 40 3+ | 80 3 | 30 2+ | 90 4 | 65 3+ | 85 4 | 75 4 | 90 4 | — |
| 15% BSA | 95 4 | 30 2 | 98 4 | 50 3 | 98 4 | 30 4 | 95 4 | 60 4 | 95 4 | 70 4 |

Freeze Time (days): [1]28, [2]28, [3]123, [4]123, [11]73

EXAMPLES 17–18

The semen of two male donors (room temp.) was diluted 1:1 with Tyrode solution (pH 7.4) and centrifuged for 15 minutes at 3500 rpm. Sperm was resuspended at a concentration of $60 \times 10^6$ per ml. of Tyrode solution. Columns were filled (glass Pasteur pipette heat sealed at point of tapering) with 1.0 ml of 6% human serum albumin. 0.5 ml of $30 \times 10^6$ sperm in Tyrode was layered over the HSA. One hour later the two layers were separated by pipette and the HSA layer prepared for freezing; HSA layers were pooled and centrifuged at 3500 rpm for 10 minutes. All but 0.3 ml of the 6% HSA was removed; 0.2 ml of freezing diluent was then added and the sperm resuspended in this mixture (0.5 ml). Sperm were then checked for motility and placed in plastic tubes (straws) for freezing at liquid nitrogen temperature (−196°). Seven minutes later the sample was rapidly thawed and motility again checked at room temperature.

| Freezing Diluent (Ingredients) | |
|---|---|
| | 100 ml |
| egg yolk | 20 ml |
| glycerin | 14 ml |
| glucose (5%) | 26.4 ml |
| sodium citrate (2.9%) | 39.6 ml |
| penicillin | 1 million units |
| streptomycin | 500 mg |
| glycine | 20 gm |

MALE NO. 1

| Fraction | Prefreeze Motility | Post-freeze Motility | Sperm Count $\times 10^6$ |
|---|---|---|---|
| Control | 65% 3 | | 180 |
| Top | 15% 2+ | | 56 |
| 6% HSA | 85% 4 | 70% 4 | 32 |

Motility of 6% HSA fraction after adding freezing diluent was 85% 4°.

MALE NO. 2

| Fraction | Prefreeze Motility | Post-freeze Motility | Sperm Count $\times 10^6$ |
|---|---|---|---|
| Control | 50% 3+ | | 99 |
| Top | 20% 3 | | 72 |
| 6% HSA | 90% 4 | 65% 4 | 20 |

Motility of 6% HSA fraction after adding freezing diluent was 80% 4°.

EXAMPLES 19–20

Bull semen from two bulls was collected in the usual manner and delivered fresh to the laboratory.
1. Bull No. 1025: Vol. 9.0 ml; 80% 4°; $900 \times 10^7$ total sperm (clean sample).
2. Bull No. 644: Vol. 3.4 ml; 85% 4°; $690 \times 10^7$ sperm (sample had considerably more sperm with separated heads and tails than did bull No. 1025).

Five glass fractionation columns 12 cm length and 13 mm internal diameter were used for each sample. Semen was fractionated at room temperature and measurements of media by volume.

Three ml of 20% BSA (in Tyrodes) were at the bottom of the glass tube; overlying were 6.0 ml of 10% BSA; and on the top was 3.0 ml of Tyrodes with bull sperm, obtained by diluting the bull semen 1:1 (bull No. 1025) or 1:2 (bull No. 644), centrifuging; and resuspending the sperm pellet in Tyrodes to a concentration of about $200 \times 10^6$ per ml. Top layer was removed after 1.0 hour; bottom two layers were removed after an additional one-half hour. Sperm recovered were checked for motility and numbers. The separated sperm (20% BSA fraction from bull No. 1025; 10% fraction from bull No. 644) were saved for freezing. The saved sperm were separated from BSA by centrifugation and resuspended in egg yolk-citrate diluent. They were cooled slowly and then mixed with glycerol for freezing using French straws (plastic tubes) in a volume of 0.5 ml. Bull No. 1025 had sperm in Tyrodes ($1 \times 10^9$/ml) as control; bull No. 644 had 1.3 ml of semen (left standing at room temperature for 4 hours) as control (mixed with 8.7 ml of diluent).

The motility of the respective fractions prior to storage are set forth below.

Bull No. 1025 121 × 10⁶ sperm/ml

| Fraction | Motility | ×10⁶ Sperm | Percent Recovery |
|---|---|---|---|
| Control | 80% 4 | 1966 | (100) |
| Top | 50% 3+ | 1204 | 61 |
| 10% | 90% 4 | 300 | 15 |
| 20% | 95% 4 | 32+ | 2 |
| | | | 78% |

+Sample frozen in 5.0 ml of diluent

Bull No. 644 216 × 10⁶ sperm/ml

| Fraction | Motility | ×10⁶ Sperm | Percent Recovery |
|---|---|---|---|
| Control | 85% 4 | 3240 | (100) |
| Top | 55% 4 | 2475 | 70 |
| 10% | 95% 4 | 600+ | 18 |
| 20% | 98% 4 | 150 | 5 |
| | | | 93% |

+Sample frozen in 5.0 ml of diluent. Both BSA fractions were free of the separated heads and tails which were prominent in the top fraction.

The adverse effect of freezing on motility is less in the case of the 10% and 20% fractions than with the unfractionated semen.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for reducing the motile sperm losses resulting from the storage of motile-sperm containing semen in a frozen state prior to use for artificial insemination purposes, which comprises (a) separating the motile sperm from the other components of the semen prior to freezing by (i) maintaining at least the sperm portion of the semen, as such or suspended in an aqueous suspending vehicle which is physiologically acceptable to the sperm and which does not substantially retard the downward migration rate of motile sperm, as an upper layer in interfacial contact, at a temperature at which the motile sperm are motile, with a lower discrete layer of an aqueous contacting medium which is physiologically acceptable to the sperm and in which the motile sperm migrate downwardly at a slower rate than in the upper layer, until at least a portion of the motile sperm of the separated sperm have migrated downwardly into the contacting medium, thereby producing a sperm fraction having a higher proportion of motile sperm than in the starting sperm, and (ii) thereafter separating the contacting medium, containing the motile sperm enhanced fraction of the starting sperm, from the upper layer; and (b) storing the separated motile sperm fraction in a frozen state.

2. A process according to claim 1 wherein the semen is human.

3. A process according to claim 2 wherein the motile sperm content of the semen is below normal.

4. A process according to claim 1 wherein the motile sperm is frozen in an aqueous vehicle physiologically acceptable to the sperm.

5. A process according to claim 4 wherein the aqueous vehicle comprises glycerin.

6. A process according to claim 5 wherein the aqueous vehicle comprises egg yolk, glucose, sodium citrate, glycine and an antibiotic.

7. A process according to claim 1 wherein the starting sperm is separated from the seminal fluid prior to being maintained in contact with the aqueous contacting medium.

8. A process according to claim 1 wherein the starting sperm is suspended in an aqueous suspending vehicle.

9. A process according to claim 1 wherein the sperm is human sperm.

10. A process according to claim 1 wherein the motile sperm which migrate to the contacting medium are thereafter separated therefrom prior to freezing.

11. A process according to claim 1 wherein the sperm portion only of the semen, suspended in an aqueous suspending vehicle, is maintained in contact with the contacting medium.

12. A process according to claim 11 wherein the sperm is human sperm.

13. A process according to claim 11 wherein the sperm is bovine sperm.

* * * * *